United States Patent [19]

Traupe et al.

[11] Patent Number: 5,759,584

[45] Date of Patent: Jun. 2, 1998

[54] METHOD FOR TREATING SKIN AFFLICTED WITH BLEMISHES OR ACNE WITH A COMPOSITION COMPRISING DISTILLED WOOL WAX ACIDS AND AT LEAST ONE MONOGLYCEROL MONOCARBOXYLIC ACID MONOESTER

[75] Inventors: Bernd Traupe, Hamburg; Uwe Schönrock, Norderstedt; Florian Wolf, Hamburg, all of Germany

[73] Assignee: Beiersdorf AG, Hamburg, Germany

[21] Appl. No.: 546,203

[22] Filed: Oct. 20, 1995

[30] Foreign Application Priority Data

Oct. 28, 1994 [DE] Germany .......................... 44 38 588.9

[51] Int. Cl.⁶ .................................................. A61K 35/12
[52] U.S. Cl. .................................... 424/520; 514/859
[58] Field of Search ........................ 424/401, 404, 424/451, 452, 489, 502, 522, 520; 514/859, 846

[56] References Cited

U.S. PATENT DOCUMENTS

| 3,711,611 | 1/1973 | Julian ................................. 514/772 |
| 4,450,175 | 5/1984 | Warshaw .............................. 514/509 |
| 4,996,193 | 2/1991 | Hewitt et al. ......................... 514/11 |
| 5,306,729 | 4/1994 | Spiegelman et al. ................. 514/546 |

OTHER PUBLICATIONS

Mosby's Complete Drug Reference: Physicians GenRx. (Mosby–Year Book: St. Louis) pp. II–1549., 1997.

Physicians' Desk Reference. (Medical Economics Data Production: Montvale, NJ) p. 1385., 1995.

*Primary Examiner*—Jean C. Witz
*Assistant Examiner*—Susan Hanley
*Attorney, Agent, or Firm*—Sprung Kramer Schaefer & Briscoe

[57] ABSTRACT

A method for treating skin afflicted with blemishes or acne with a composition comprising distilled wool wax acids and at least one monoglycerol monocarboxylic acid monoester is presented.

5 Claims, No Drawings

METHOD FOR TREATING SKIN AFFLICTED WITH BLEMISHES OR ACNE WITH A COMPOSITION COMPRISING DISTILLED WOOL WAX ACIDS AND AT LEAST ONE MONOGLYCEROL MONOCARBOXYLIC ACID MONOESTER

A method for treating skin afflicted with blemishes or acne with a composition comprising distilled wool wax acids and at least one monoglycerol monocarboxylic acid monoester

BACKGROUND OF THE INVENTION

The present invention relates to active compounds and formulations comprising such active compounds which are active against blemished skin.

In addition to other influences, bacterial secondary infections are of etiological importance to blemished skin. One of the most important microorganisms associated with blemished skin is Propionibacterium acnes.

Blemished skin and/or comedones impair the well-being of those affected even in mild cases. Since practically every adolescent is affected-by blemished skin to some degree, there is the need to remedy this state in many persons.

SUMMARY OF THE INVENTION

The object of the present invention was thus to discover a substance which is active against blemished skin or Propionibacterium acnes.

It has been found, surprisingly, and therein lies the achievement of all these objects, that the disadvantages of the prior art are remedied by the use of active compound combinations of (I) a naturally occurring mixture of wool wax acids or a mixture of wool wax acids processed by distillation and (II) monoglycerol monocarboxylic acid monoesters or formulations comprising such active compound combinations against blemished skin, mild forms of acne and Propionibacterium acnes.

DETAILED DESCRIPTION OF THE INVENTION

Wool wax or wool fat is the fat-like to waxy constituent of raw sheep's wool obtained in washing of raw wool. Wool wax comprises a mixture of fatty acid esters of higher alcohols and free fatty acids.

The main constituents of wool wax acids are (a) saturated unsubstituted carboxylic acids according to the formula $$CH_3-(CH_2)-CH_2-COOH,$$

(b) α-hydroxycarboxylic acids according to the formula

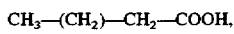

(c) ω-hydroxycarboxylic acids according to the formula $$HO-CH_2-(CH_2)-CH_2-COOH,$$

(d) isocarboxylic acids according to the formula

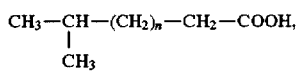

(e) α-hydroxy-isocarboxylic acids according to the formula

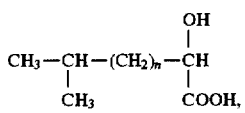

(f) ω-hydroxy-isocarboxylic acids according to the formula

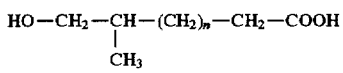

(g) anteisocarboxylic acids according to the formula

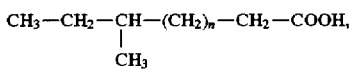

(h) α-hydroxy-anteisocarboxylic acids according to the formula

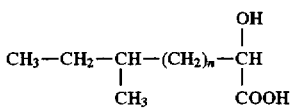

(i) ω-hydroxy-anteisocarboxylic acids according to the formula

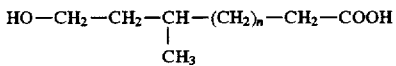

n here usually assumes values of 7–31. Representative compositions of wool wax acids are described for example in "Parfümerie und Kosmetik" ("Perfumes and cosmetics"), Volume 59, No. 12/78, pages 429, 430 and in "Lexikon der Hilfsstoffe für Pharmazie, Kosmetik und angrenzende Gebiete" ("Dictionary of auxiliaries for pharmacy, cosmetics and related fields") by H. P. Fiedler, 1989, 3rd edition, Editio Cantor Aulendorf.

Raw wool wax acids are unsuitable for cosmetic purposes, and instead of these distilled wool wax acids are usually employed. This state of affairs and corresponding processes for refining the raw wool wax acids are known to the expert.

Particularly advantageous processes for working up raw wool wax acid are to be found, for example, in EP Laid-Open Specification 556 660.

Wool wax acids typically comprise about 60% of saturated, unsubstituted carboxylic acids, about 30% of α-hydroxycarboxylic acids and about 5% of ω-hydroxycarboxylic acids, the remainder of about 5% essentially being formed by the other abovementioned types of carboxylic acids.

A wool wax acid fraction obtainable from raw wool wax acid by molecular distillation in vacuo under $10^{-1}$ bar from the distillation temperature range of 150°–200° C. is particularly advantageous according to the invention. The content of α-hydroxycarboxylic acids here is about 22–27%. Such fractions are distinguished by the following characterizing parameters:
Drop point: 50°–54° C.
Acid number: 166–170
Saponification number: 175–190
OH number: 60–80
Iodine value: 7–12

It is indeed known from the paper "Antimicrobial Factors in Wool Wax" (Australian Journal of Chemistry, 1971, 24, pages 153 et seq.) that some wool wax batches comprise antimicrobial factors. However, there is no indication in the direction of the present invention in the reference mentioned.

The monoglycerol monocarboxylic acid monoesters (occasionally also called monocarboxylic acid monoglycerides in this specification) according to the invention are represented by the general formula

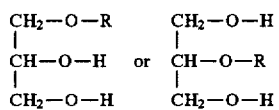

wherein R is a branched or unbranched acyl radical having 6–14 carbon atoms. R is advantageously chosen from the group consisting of unbranched acyl radicals. The fatty acids or monocarboxylic acids on which these esters are based are
hexanoic acid (caproic acid) ($R = -C(O) - C_5H_{11}$),
heptanoic acid (oenanthic acid) ($R = -C(O) - C_6H_{13}$),
octanoic acid (caprylic acid) ($R = -C(O) - C_7H_{15}$),
nonanoic acid (pelargonic acid) ($R = -C(O) - C_8H_{17}$),
decanoic acid (capric acid) ($R = -C(O) - C_9H_{19}$),
undecanoic acid ($R = -C(O) - C_{10}H_{21}$),
dodecanoic acid (lauric acid) ($R = -C(O) - C_{11}H_{23}$),
tridecanoic acid ($R = -C(O) - C_{12}H_{25}$)
tetradecanoic acid (myristic acid) ($R = -C(O) - C_{13}H_{27}$).

R is particularly advantageously the octanoyl radical (caprylic acid radical) or the decanoyl radical (capric acid radical), that is to say is represented by the formulae $$R = -C(O) - C_7H_{15}$$

or $$R = -C(O) - C_9H_{19}$$

In this specification, especially in the examples, the abbreviation GMCy is used for glycerol monocaprylate and the abbreviation GMC is used for glycerol monocaprate.

In the case of the glycerol esters esterified in the 1-position of the glycerol, the 2-position is a centre of asymmetry. The 2S and the 2R configurations are active according to the invention and are equally advantageous.

It has proved favourable to use racemic mixtures of the stereoisomers.

The content of GMCy and/or GMC in the cosmetic or dermatological formulations according to the invention is advantageously 0.1–10.0% by weight, preferably 0.5 to 7.5% by weight, particularly preferably 1.5–5.0% by weight, in each case based on the total weight of the particular formulation.

It is indeed known per se that some glycerol esters of saturated fatty acids per se, in particular the glycerol monolaurate, but also glycerol monocaprylate and glycerol monocaprate which are advantageous according to the invention, display an antimicrobial action.

A cosmetic with antiseptic properties which is distinguished by a content of caprylic acid monoglyceride is thus known, for example, from JP Laid-Open Specification Sho-48/019940 from Taiyo Kagaku Kogyo Co. Ltd.

Finally, EP Laid-Open Specification 530 861 describes topical antimicrobial pharmaceutical combinations also comprising, in addition to glycerol monocaprylate and glycerol monocaprate, a mixture of saturated fatty acids which, however, in contrast to the main constituents of the wool wax acid mixtures according to the invention, are unsubstituted and therefore could give no indication of the present invention.

It was surprising, however, that the active compound mixtures according to the invention are distinguished by an outstanding action against blemished skin or Propionibacterium acnes.

In fact, it was not foreseeable that the active compound mixtures according to the invention are capable of reaching the facultatively anaerobic Propionobacteria in the lower layers of skin at all.

In the clinical picture of acne or blemished skin, the Propionobacteria additionally attacks the hair follicles, which are sealed from the top by a dense lipid plug. As the expert knows, this is the main obstacle to many substances which are potentially active against Propionobacteria being employed against acne or blemished skin, since the substances in question simply do not have suitable penetration properties.

The use of an active compound mixture comprising
(I) a naturally occurring wool wax acid mixture or a wool wax acid mixture obtainable by distillation and
(II) glycerol monocaprylate and/or glycerol monocaprate, for combating the clinical picture of blemished skin, mild forms of acne and Propionobacterium acnes is regarded as a particularly advantageous embodiment of the present invention.

It is advantageous to choose the content of (i) wool wax acid mixture and (ii) monoglycerol monocarboxylic acid monoester such that ratios of (i):(ii) of 5:1 to 1:20, in particular about 1:10, particularly advantageously about 1:5, result.

It is particularly advantageous to choose the content of (i) wool wax acids and (ii) glycerol monocaprylate and/or glycerol monocaprate such that ratios of (i):(ii) of 5:1 to 1:20 result. Ratios of (i):(ii) of 5:1 to 1:5, in particular about 1:1, particularly advantageously about 1:3, are particularly favourable in the context of the present invention.

Formulations according to the invention which comprise active compound combinations according to the invention are particularly advantageously characterized in that the active compound combinations according to the invention are present in concentrations of 0.05–10.00%. by weight, preferably 0.1–5.0% by weight, in each case based on the total weight of the formulations.

The formulations according to the invention which are active against blemished skin can be in the form of liquid compositions which can be applied by means of brushes or spreaders or roll-on devices, in the form of sticks, and in the form of W/O or O/W emulsions, for example creams or lotions, which can be applied from customary bottles and containers. The formulations according to the invention which are active against blemished skin can furthermore advantageously be in the form of face lotions, tinctures or cleansing formulations.

The formulations according to the invention which are active against blemished skin can also be in the form of aerosols, that is to say preparations which can be sprayed from aerosol containers, squeeze bottles or by a pump device, or in the form of liquid compositions which can be applied by means of roll-on devices, in the form of sticks and in the form of W/O or O/W emulsions, for example creams or lotions, which can be applied from normal bottles and containers. It is furthermore advantageous to use hydrodispersions or gels as carriers for the active compound combinations according to the invention.

The formulations according to the invention which are active against blemished skin can furthermore also advantageously be in the form of tinctures, shampoos, shower or bathing formulations, powders or powder sprays.

As customary cosmetic carriers for the preparation of the formulations according to the invention, in addition to water, ethanol and isopropanol, glycerol and propylene glycol, it is possible to employ skin care fatty or fat-like substances, such as decyl oleate, cetyl alcohol, cetylstearyl alcohol and 2-octyldodecanol, in the ratios of amounts customary for such preparations, as well as swelling agents and thickeners, for example hydroxyethyl- or hydroxypropylcellulose, polyacrylic acid or polyvinylpyrrolidone, and in addition, but also in small amounts, cyclic silicone oils (polydimethylsiloxanes), as well as liquid polymethylphenylsiloxanes of low viscosity.

Suitable propellants for formulations according to the invention which can be sprayed from aerosol containers are the customary known, readily volatile, liquefied propellants, for example hydrocarbons (propane, butane or isobutane), which can be employed by themselves or as a mixture with one another. Compressed air can also advantageously be used.

The expert of course knows that there are propellant gases which are non-toxic per se and would be suitable in principle for the present invention, but which should nevertheless be omitted because of an unacceptable action on the environment or other concomitant circumstances, in particular chlorofluorocarbons (CFCs).

Emulsifiers, which can be used in the formulations in a small amount, for example 2 to 5% by weight, based on the total composition, and which have proved suitable for preparation of the formulations according to the invention, which are advantageously to be applied to the desired areas of skin as liquid formulations by means of a roll-on device, are nonionic types, such as polyoxyethylene fatty alcohol ethers, for example cetostearyl alcohol polyethylene glycol ethers having 12 or 20 ethylene oxide units added on per molecule, cetostearyl alcohol and sorbitan esters and sorbitan esterethylene oxide compounds (for example sorbitan monostearate and polyoxyethylene sorbitan monostearate), and long-chain, higher molecular weight, waxy polyglycol ethers.

In addition to the constituents mentioned, perfume, dyes, antioxidants, suspending agents, buffer mixtures or other customary cosmetic base substances can be added to the formulations according to the invention, the pH of which is preferably brought to 4.0 to 9.0, in particular 5.0 to 6.5, for example, by customary buffer mixtures.

The pH of the cosmetic formulations according to the invention is preferably adjusted such that the acid components according to the invention are essentially present as acids, and not as anions, that is to say preferably in the acid to neutral range, in particular in the pH range of 5.0–6.5.

All the antioxidants suitable or customary for cosmetic and/or dermatological uses can be used according to the invention as favourable antioxidants.

The antioxidants are advantageously chosen from the group consisting of amino acids (for example glycine, histidine, tyrosine and tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones and penta-, hexa- and heptathionine-sulphoximine) in very low tolerated dosages (for example pmol to μmol/kg), and furthermore (metal)chelators (for example α-hydroxy-fatty acids, palmitic acid, phytic acid or lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example γ-linolenic acid, linoleic acid and oleic acid), folic acid and derivatives thereof, ubiquinone and ubiquinol and derivatives thereof, vitamin-C and derivatives (for example ascorbyl palmitate, Mg ascorbyl phosphate and ascorbyl acetate), tocopherols and derivatives (for example vitamin E acetate), vitamin A and derivatives (vitamin A palmitate) and coniferyl benzoate of gum benzoin, rutic acid and derivatives thereof, ferulic acid and derivatives thereof, butylated hydroxy-toluene, butylated hydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO and $ZnSO_4$), selenium and derivatives thereof (for example selenomethionine), stilbenes and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

The amount of antioxidants (one or more compounds) in the formulations is preferably 0.001 to 30% by weight, particularly preferably 0.05–20% by weight, in particular 1–10% by weight, based on the total weight of the formulation.

If vitamin E and/or derivatives thereof are the antioxidant or antioxidants, it is advantageous to choose the particular concentrations thereof from the range of 0.001–10% by weight, based on the total weight of the formulation.

If vitamin A or vitamin A derivatives or carotenes or derivatives thereof are the antioxidant or antioxidants, it is advantageous to choose the particular concentrations thereof from the range of 0.001–10% by weight, based on the total weight of the formulation.

The amounts of cosmetic or dermatological carrier substances and perfume to be employed in each case can easily be determined by the expert according to the nature of the particular product by simple trial and error.

For perfuming, if desired, those substances and perfume oils which are stable, do not irritate the skin and already have antibacterial or bacteriostatic properties as such are also suitable, where appropriate.

Apart from special formulations which are noted separately in each case in the examples, the formulations according to the invention are prepared in the customary manner, usually by simple mixing with stirring, if appropriate with gentle heating. The preparation presents no difficulties. For emulsions, the oily phase and the aqueous phase are prepared separately, for example, if appropriate with heating, and are then emulsified.

The customary rules, with which the expert is familiar, for compiling cosmetic formulations are otherwise to be observed.

If the combinations according to the invention are to be incorporated into powder sprays, the suspension bases for this can advantageously be chosen from the group consisting of silicic acid gels (for example those which are obtainable under the tradename Aerosil®), kieselguhr, talc, modified starch, titanium dioxide, silk powder, nylon powder, polyethylene powder and related substances.

Advantageous embodiment examples of the present invention follow. The numerical values stated are always % by weight, unless expressly stated otherwise. In the examples, the term "WWA" means a wool wax acid fraction which has been obtained from raw wool wax acid by molecular distillation in vacuo under $10_{-1}$ bar from the distillation temperature range of 150°–200° C. The content of α-hydroxycarboxylic acids here is about 22–27%.

EXAMPLE 1

Roll-on gel I–III

|  | I | II | III |
| --- | --- | --- | --- |
| PEG-40 hydrogenated castor oil | 1.75 | 1.50 | 1.75 |
| WWA | 0.40 | 0.40 | 0.40 |
| GMC | 0.75 | 0.60 | — |
| GMCy | — | — | 0.90 |
| Ethanol | 62.00 | 62.00 | 60.00 |
| Perfume | q.s. | q.s. | q.s. |
| Water, completely deionized - in each case to 100.00 - | | | |

EXAMPLE 2

Roll-on emulsion I–III

|  | I | II | III |
| --- | --- | --- | --- |
| PEG-21 stearyl ether (Brij 721) | 1.50 | 1.60 | 1.50 |
| PEG-2 stearyl ether (Brij 72) 2.50 | 2.80 | 2.50 | |
| Mineral oil DAB 9 | 4.00 | 4.50 | 4.00 |
| Isopropyl palmitate | 3.50 | 3.50 | 4.00 |
| Methyl/propyl-paraben | 0.15 | 0.15 | 0.15 |
| WWA | 0.70 | 0.70 | 0.70 |
| GMC | 0.70 | — | 0.50 |
| GMCy | — | 0.90 | — |
| Perfume | q.s. | q.s. | q.s. |
| Water, completely deionized - in each case to 100.00 - | | | |

EXAMPLE 3

Pump spray I–II

|  | I | II |
| --- | --- | --- |
| Ethanol | 68.00 | 60.00 |
| 1,2-Propylene glycol | 1.80 | 1.80 |
| WWA | 0.30 | 0.30 |
| GMC | 0.70 | — |
| GMCy | — | 1.1 |
| Perfume | q.s. | q.s. |
| Water, completely deionized - in each case to 100.00 - | | |

EXAMPLE 4

Gel stick I–II

|  | I | II |
| --- | --- | --- |
| Stearic acid | 6.00 | 6.00 |
| Ceteareth-15 | 2.75 | 2.75 |
| WWA | 2.00 | 2.00 |
| GMC | 1.50 | — |
| GMCy | — | 1.60 |
| Ethanol | 16.00 | 16.00 |
| NaOH | 1.10 | 1.05 |
| Perfume | q.s. | q.s. |
| Water, completely deionized - in each case to 100.00 - | | |

EXAMPLE 5

Deodorant cream I–II

|  | I | II |
| --- | --- | --- |
| Mineral oil DAB 9 | 3.50 | 3.50 |
| PEG-40 stearate | 4.00 | 4.00 |
| Cetyl alcohol | 3.50 | 3.50 |
| Ethylhexyl stearate | 0.90 | 0.90 |
| Propylene glycol | 1.00 | 1.00 |
| Methyl/propyl-paraben | 0.15 | 0.15 |
| WWA | 0.30 | 0.30 |
| GMC | 0.60 | — |
| GMCy | — | 1.1 |
| Perfume | q.s. | q.s. |
| Water, completely deionized - in each case to 100.00 - | | |

We claim:

1. A method of treating skin afflicted with blemishes or acne comprising applying to said skin an amount sufficient treat said skin effectively of a composition comprising as active ingredients:

a) a wool wax acid mixture obtained by distillation having the following properties:

| Drop point | 50–54° C. |
| --- | --- |
| Acid number | 166–170° C. |
| Saponification number | 175–190° C. |
| OH number | 60–80 |
| Iodine value | 7–12; and |

2. The method according to claim 1, wherein said composition comprising said active ingredients is a cosmetic or dermatological composition.

3. The method according to claim 1, wherein the wool wax acid mixture is obtained from raw wool wax by molecular distillation of said wool wax in vacuo under $10^{-1}$ bar over a temperature range of 150°–200° C.

4. The method according to claim 1, wherein monoglycerol monocarboxylic acid monoester is chosen from the group consisting of glycerol monocaprylate and glycerol monocaprate.

5. The method according to claim 1, which is for treating skin afflicted with acne, wherein said acne is a Propionibacterium acne.

* * * * *

UNITED STATES PATENT AND TRADEMARK OFFICE
CERTIFICATE OF CORRECTION

PATENT NO. : 5,759,584
DATED : June 2, 1998
INVENTOR(S) : Traupe, et al.

It is certified that error appears in the above-identified patent and that said Letters Patent is hereby corrected as shown below:

<u>Column 8, claim 4,</u>
Line 1, after "wherein" insert -- the --.
Line 46, after "and" on a new line insert --b)at least one monoglycerol monocarboxylic acid monoester --.

Signed and Sealed this

Twelfth Day of February, 2002

Attest:

JAMES E. ROGAN
*Attesting Officer*     *Director of the United States Patent and Trademark Office*